(12) United States Patent
Mao et al.

(10) Patent No.: US 8,530,194 B2
(45) Date of Patent: Sep. 10, 2013

(54) OLIGONUCLEOTIDES AS TEMPERATURE-SENSITIVE INHIBITORS FOR DNA POLYMERASES

(75) Inventors: Fei Mao, Fremont, CA (US); Xing Xin, Foster City, CA (US)

(73) Assignee: AlleLogic Biosciences Corporation, Hayward, CA (US)

( * ) Notice: Subject to any disclaimer, the term of this patent is extended or adjusted under 35 U.S.C. 154(b) by 945 days.

(21) Appl. No.: 12/088,213

(22) PCT Filed: Sep. 26, 2006

(86) PCT No.: PCT/US2006/037238
§ 371 (c)(1),
(2), (4) Date: Aug. 29, 2008

(87) PCT Pub. No.: WO2007/038422
PCT Pub. Date: Apr. 5, 2007

(65) Prior Publication Data
US 2009/0047714 A1      Feb. 19, 2009

Related U.S. Application Data

(60) Provisional application No. 60/721,138, filed on Sep. 26, 2005.

(51) Int. Cl.
*C12P 19/34* (2006.01)
*G01N 33/53* (2006.01)

(52) U.S. Cl.
USPC .......................................... 435/91.1; 435/7.1

(58) Field of Classification Search
USPC ...................... 536/23.1, 24.33; 435/91.1, 7.1
See application file for complete search history.

(56) References Cited

U.S. PATENT DOCUMENTS

| | | | |
|---|---|---|---|
| 5,413,924 A | 5/1995 | Kosak et al. | |
| 6,403,341 B1 | 6/2002 | Barnes et al. | |
| 6,830,902 B1 * | 12/2004 | Astatke et al. | 435/91.1 |

FOREIGN PATENT DOCUMENTS

| | | | |
|---|---|---|---|
| WO | WO 01/02559 A1 | | 1/2001 |
| WO | WO 0102559 | * | 1/2001 |

OTHER PUBLICATIONS

Dang, et al. Oligonucleotide inhibitors of Taq DNA polymerase facilitate detection of low copy number targets by PCR.. Journal of Molecular Biology. 1996; 264(2):268-278.
Frohman, et al. Rapid production of full-length cDNAs from rare transcripts: amplification using a single gene-specific oligonucleotide primer. Proc Natl Acad Sci U S A. Dec. 1988;85(23):8998-9002.
Harrington et al., "The characterization of a mammalian DNA structure-specific endonuclease," The EMBO Journal, vol. 13(5), pp. 1235-1246, 1994.
Horton, et al. AmpliGrease: "hot start" PCR using petroleum jelly. Biotechniques. Jan. 1994;16(1):42-3.
International search report and written opinion dated Sep. 25, 2007 for PCT Application No. US2006/037238.

* cited by examiner

*Primary Examiner* — Cynthia Wilder
(74) *Attorney, Agent, or Firm* — Wilson Sonsini Goodrich & Rosati

(57) ABSTRACT

Aspects of the invention relate to the use of novel oligonucleotides as temperature-sensitive inhibitors for thermostable DNA polymerases. Some inhibitors exhibit temperature-dependent and, in some cases, reversible inhibitory property by changing the conformation of at least a portion of the oligonucleotides from double-stranded to single stranded or in some cases vice versa in a temperature-dependent manner. Aspects also relate to the use of an the inhibitors in a hot-start PCR compositions, wherein the inhibitor may act to suppress the activity of the thermostable DNA polymerase below a desired activation temperature, Tact, and wherein the inhibitor is thermally inactivated above Tact, thus liberating the polymerase activity and initiating the DNA amplification process. Aspects further relate to a procedure for formulating the composition of a hot-start PCR reaction mixture. The hot-start PCR methods disclosed herein are generally faster, more flexible and lower in cost than existing methods.

10 Claims, 7 Drawing Sheets

FIG. 1. DNA Polymerase Exhibits Two Distinct Conformations
A
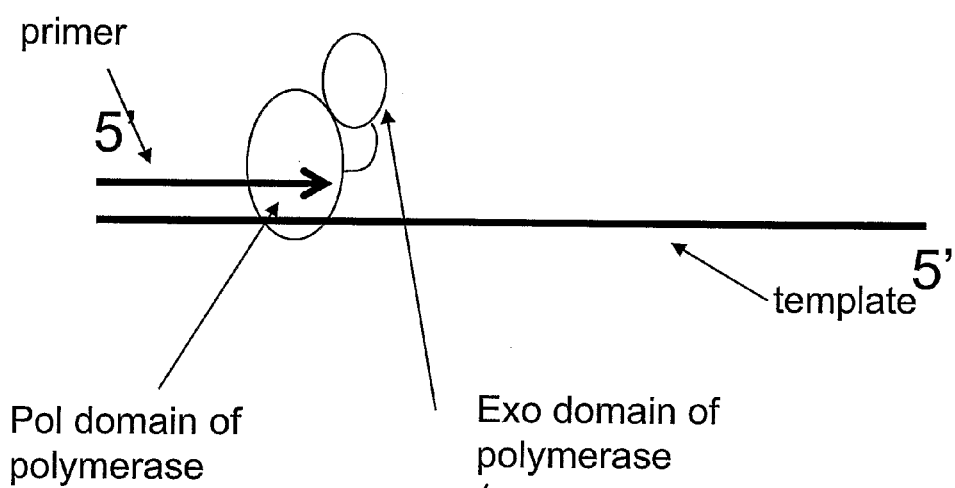
B
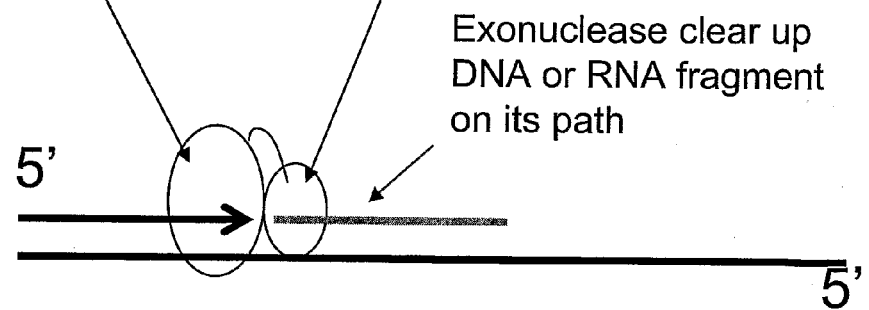

FIG 2. Secondary structures of inhibitors
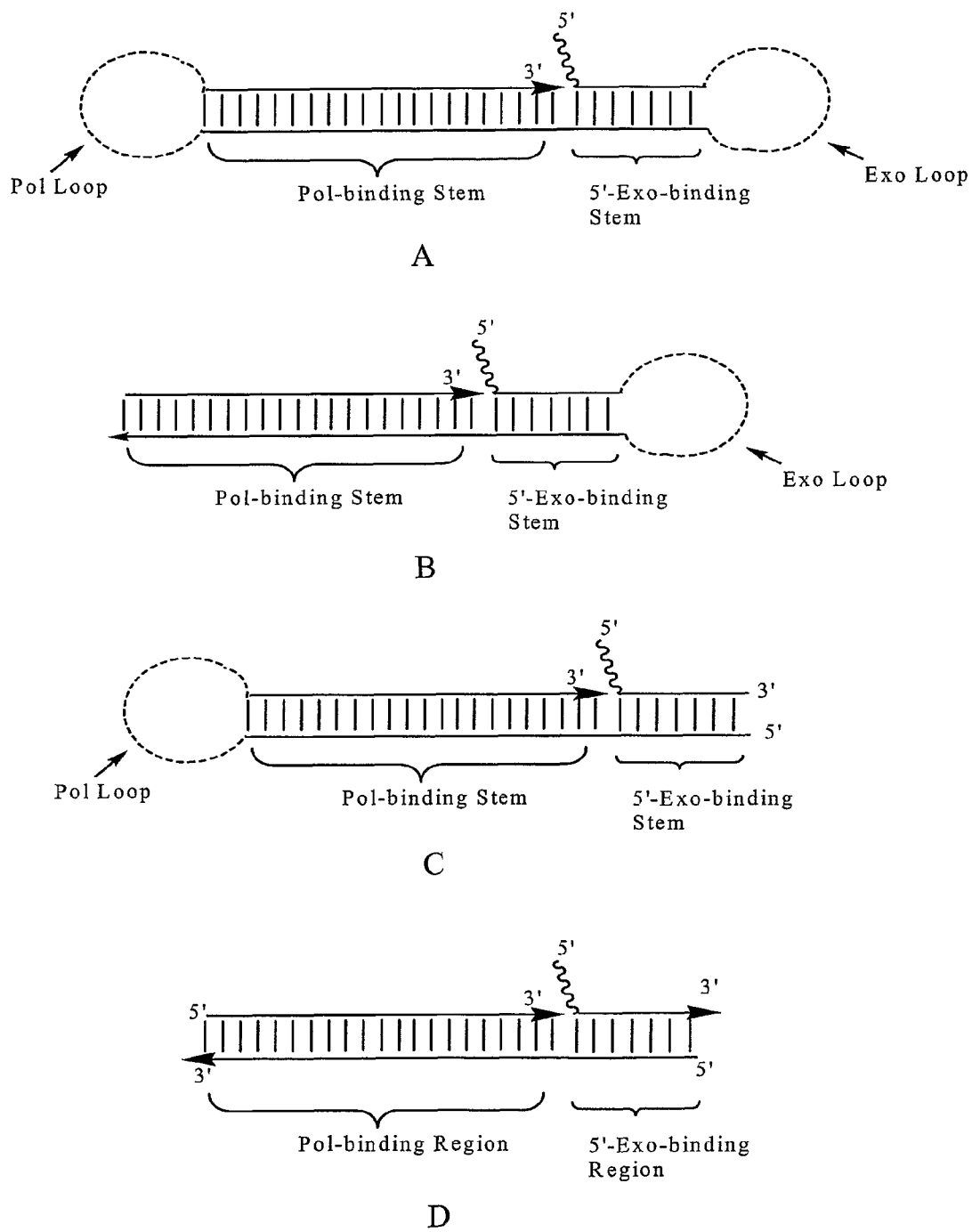

FIG. 3 Under High Temperatures, Exo binding stem melts. 5' exonuclease domain will shift away from the template
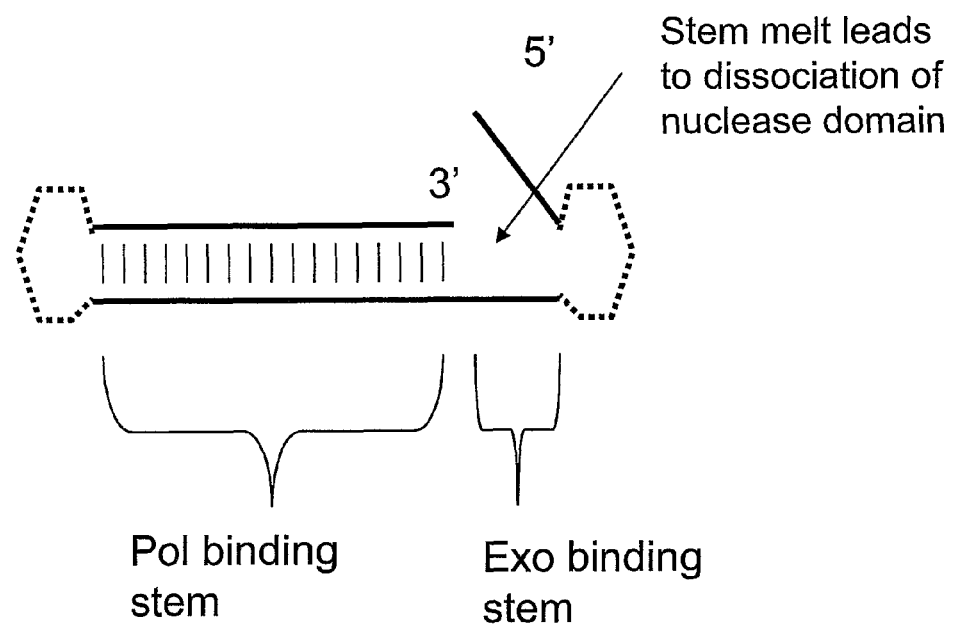

FIG 4. Examples of Hot Start PCR Reaction
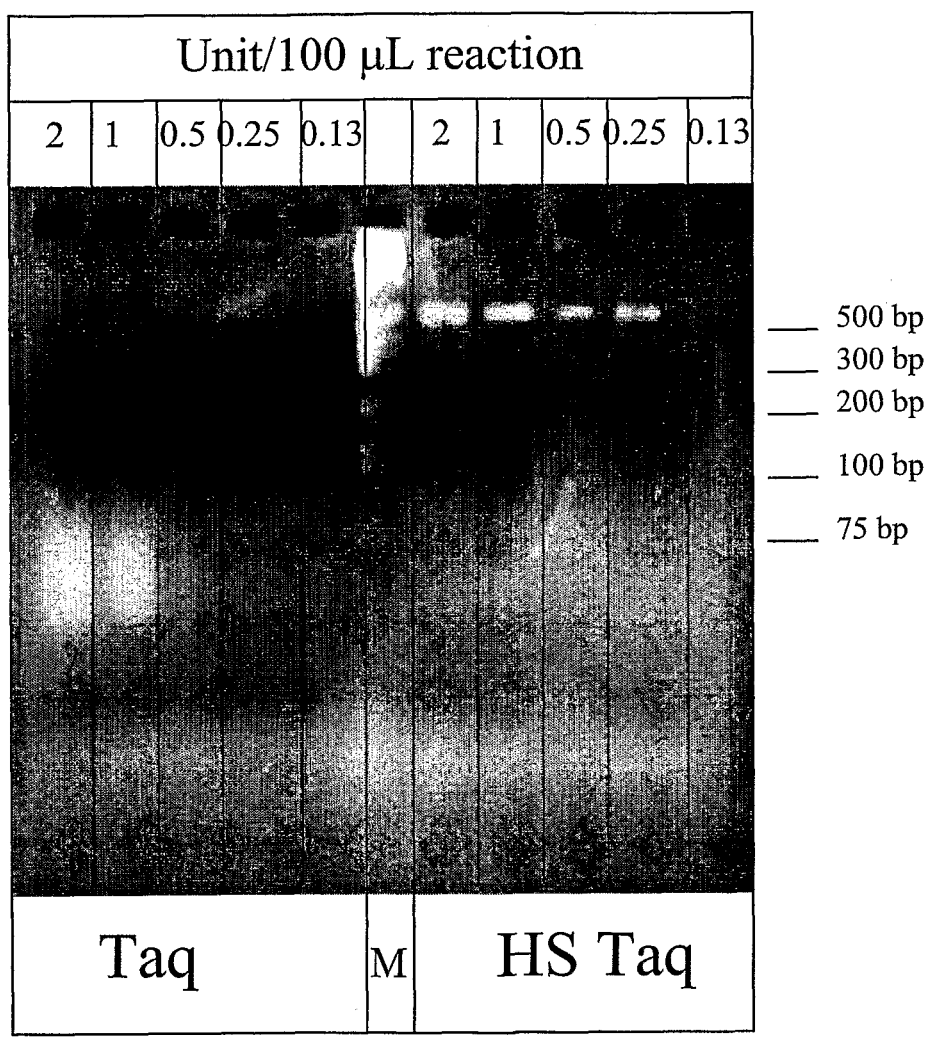
M: DNA molecular weight marker
(1 kb ladder from Invitrogen)

Performance in real time PCR

FIG. 7. Schematic Diagrams Of Some Primary Structures
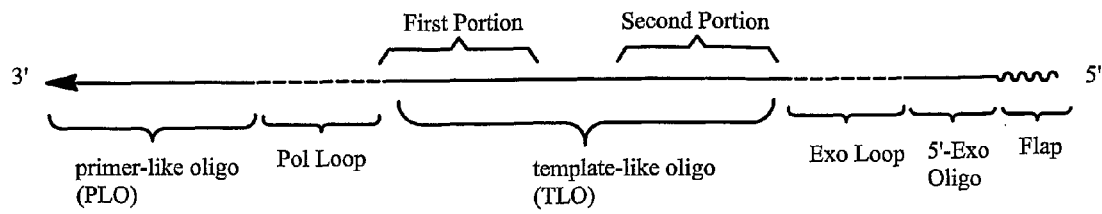
Formula 1
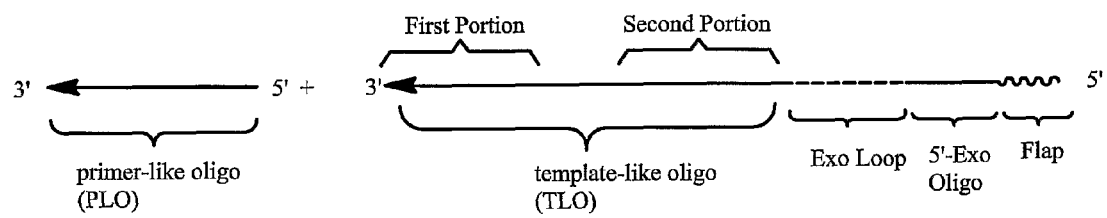
Formula 2
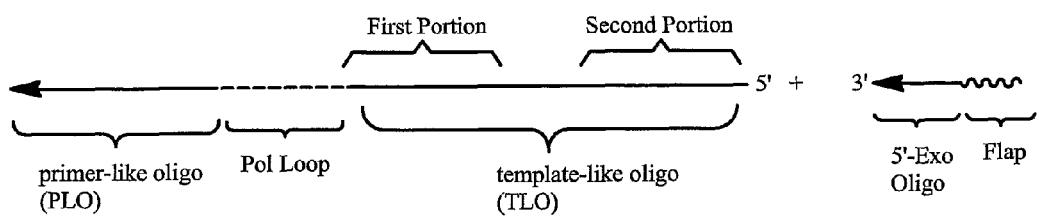
Formula 3
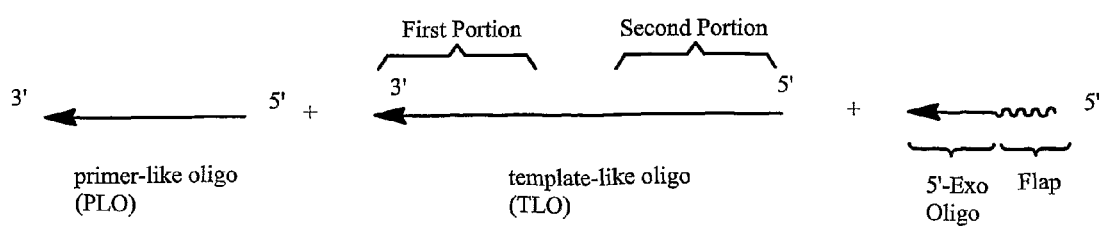
Formula 4

OLIGONUCLEOTIDES AS TEMPERATURE-SENSITIVE INHIBITORS FOR DNA POLYMERASES

PRIORITY CLAIM

This application claims the benefit of U.S. Provisional Patent Application Ser. No. 60/721,138 filed on Sep. 26, 2005, which is incorporated herein by reference in its entirety.

FIELD OF THE INVENTION

The present invention generally relates to oligonucleotides. In particular, it relates to the use of oligonucleotides as temperature-sensitive inhibitors of DNA polymerases.

BACKGROUND OF THE INVENTION

Polymerase chain reaction (PCR) is a primer extension reaction that provides a method for amplifying specific nucleic acids in vitro. Widely used for cloning and other molecular biological manipulations (Mullis et al., 1987, Methods Enzymol.; Saiki et al., 1985, Science), the method can produce a million to a billion fold copies of a DNA template in a single enzymatic reaction within a matter of minutes to hours, enabling researchers to determine the size and sequence of a target DNA.

Despite significant progress, improvements in several areas of PCR technology are still needed. One particular area concerns non-specific DNA amplification due to mis-priming. During a PCR reaction, the particular stretch of DNA to be amplified, called the target sequence, is identified by a specific pair of oligonucleotides called primers. The specificity of DNA amplification typically depends on the specificity of primer-target hybridization, which is usually reflected by the melting points, $T_m$, of the primer-target hybrids and is also affected by the temperature at which the primer extension reaction takes place. In general, more specific primer-target hybridization occurs at higher temperatures, typically 50-70° C. Since the chain extension step of a PCR reaction is usually carried out within this temperature range, during which Taq is also most active, nonspecific DNA amplifications are mostly minimized. On the other hand, so-called mis-priming, which results from primer hybridizing to partially complimentary sequences or to other primers, takes place more frequently at lower temperatures such as room temperature. Another problem is that Taq still has significant residual activity at room temperature although the enzyme exhibits the highest activity in the normal PCR temperature range of 50-70° C. The partially or weakly hybridized primers coupled with the residual Taq activity at a lower temperature such as room temperature could lead to significant formation of nonspecific amplification products. When the temperature is elevated to 50-70° C. to initiate a PCR reaction, these non-specific products formed at the lower temperature sometimes now act as templates and compete with the amplification of the desired product, thus leading to even greater amount of nonspecifically amplified products. Since a PCR reaction is usually first assembled at room temperature, it is therefore highly desirable and in some cases essential to suppress any polymerization activity at lower temperatures such as room temperature before the desired amplification reaction takes place at higher temperatures.

To overcome the aforementioned problem, various so-called "hot-start" PCR methods have been developed that allow one to turn off the amplification reaction at room temperature and to turn on when the temperature is raised to the normal PCR operating temperature range. In general, nearly all known hot-start methods employ a strategy of suppressing the polymerase activity at below the PCR temperature range.

One earlier hot-start method involves withholding one or more components of a PCR reaction until the reaction vessel is heated to the PCR operating temperature (U.S. Pat. No. 6,403,341, Barnes et al., Frohman M A et al, PNAS (1998) 85:8998-9002). Although the method is conceptually straight forward, the extra step required for reagent mixing is not only inconvenient but also susceptible to contamination and incompatible with high throughput operations.

Another earlier version of hot-start method suppresses the polymerase activity by creating a temperature-dependent physical barrier, such as the use of wax, to separate the PCR components (U.S. Pat. Nos. 5,413,924, Horton et al., Biotechniques 16:42-43). As an example, Taq DNA polymerase can be stored in wax beads while the rest of the PCR components are left in the aqueous phase. When the reaction vessel is heated to the denaturing temperature of PCR, usually above 90° C., the wax melts, thus mixing all components. However, since mixing of the components relies largely on heat convection, which is most likely inefficient and incomplete in view of the designs of most of the commercial PCR instruments, this method is again not widely used.

Most of the commercially available hot-start polymerases, or so-called master-mixes that contain all necessary components to start a PCR except for the primers and template, now employ a pre-mixed and single-phased format that avoids manual reagent addition and convection-based reagent mixing.

One strategy of developing a hot-start polymerase is to chemically modify the enzyme, more specifically, the lysine residues of the enzyme, with a thermally unstable chemical group to inactivate the enzyme. Once the reaction is heated to temperatures above 90° C. for 10 to 20 minutes, the heat-labile modifying group is cleaved from the enzyme, thus re-activating the enzyme activity. (U.S. Pat. Nos. 5,677,152 and 6,183,998). There are a couple of major drawbacks with this method. First, since there are multiple lysine residues in the enzyme, the modification reaction is difficult to control, typically resulting in a complex mixture of labeled enzyme with some enzyme molecules more heavily labeled and others lightly labeled. Accordingly, the temperature response of the modified enzyme molecules is often heterogeneous with the lightly labeled enzyme molecules more easily re-activated but the more heavily labeled enzyme molecules more difficult to be reactivated. Second, the yield for making the modified enzyme is relatively low, typically in the range of 10 to 50%, which, when coupled with the relatively high cost of the enzyme itself, can make this method uneconomical. Finally, it is desirable to shorten the 10- to 20-minutes enzyme activation time, which makes up a significant portion of the overall PCR time with this method.

Another hot-start PCR method employs polymerase-specific monoclonal antibodies to inhibit the enzyme activity. Often an antibody to enzyme molar ratio of seven to one is used to sufficiently inactivate the enzyme. The monoclonal antibodies bind to the polymerase at lower temperatures such as room temperature in a manner to inactivate the enzyme. When the reaction temperature is raised above 90° C., the antibodies lose affinity for the enzyme, which therefore becomes reactivated again. (U.S. Pat. No. 5,338,671, Scalice E R et al, Kellogg et al, (1994) Biotechniques 16:1134-1137). One advantage of this method is that the enzyme activation time is only 1 to 3 minutes, a significant improvement over the chemically modified enzyme method. However, a major drawback with this method is the relatively high cost associated with the use of a large amount of antibody molecules.

Still another hot-start PCR method employs negatively charged polymers to block polymerase as disclosed in the US. Pat. Application No. US2003/0092135A1. The negatively charge polymers exhibit temperature-dependent inhibition to Taq DNA polymerase activity with high inhibition at low temperatures and low or no inhibition at high temperatures.

Other variations of negatively charge polymers have also been used to inhibit DNA polymerase activity. For example, short DNA fragments (Kainz P. et al (2000) BioTechniques 28:278-282, also U.S. Pat. No. 6,830,902B1) or aptamers (U.S. Pat. No. 5,693,502) have been used to formulate hot-start PCR reactions. These oligonucleotide-based inhibitors bind to a DNA polymerase by mimicking the natural substrate of the enzyme. At elevated temperatures, the inhibitors lose their binding affinity for the enzyme, rendering polymerase available to its normal substrate. However, in order to achieve complete enzyme inhibition at lower temperatures, the concentration of the inhibitors typically needs to be in the hundreds of micromole range so that they can compete effectively for enzyme binding with the natural substrate. Although the hot-start method using these inhibitors also has the advantage of relatively short enzyme activation time, typically within a minute, the high cost of having to use a large quantity of the inhibitors makes this technology unpractical.

Still there remains a need for a hot-start PCR method that is single-phased, fast to hot-start, low cost and easy to handle all at the same time. As disclosed herein, various aspects of the present invention address these objectives.

SUMMARY OF THE INVENTION

Some embodiments of the present invention are directed to the use of oligonucleotides as inhibitors for DNA polymerases, and some embodiments relate to methods and compositions for performing hot-start PCR reactions to improve amplification specificity. These novel embodiments offer a simple and cost effective alternative to previous hot-start PCR methods. One embodiment of the present invention includes the use of a competitive inhibitor that binds to both the Pol domain and the exonuclease domain of a thermostable DNA polymerase to control the activity of the enzyme in a temperature-dependent manner.

One embodiment is a DNA polymerase inhibitor suitable for binding to a DNA polymerase which includes a Pol domain and a 5'-exo domain of a DNA, the inhibitor may include at least one oligonucleotide, in which the oligonucleotide includes a first section of DNA, and a second section of DNA, wherein the first section of DNA forms a double stranded DNA structure that binds to the Pol domain of a DNA polymerase, and the second section of DNA forms a double stranded structure that binds to the 5'-exo domain of the DNA polymerase, the second section may also include at least at least two nucleotides joined by a backbone linkage in which at least one of the backbone linkages in or near the 5'-exo oligo is resistant to 5-exonyclease activity.

In one embodiment a DNA polymerase inhibitor includes a primer-like oligo of between about 8- to about 50-oligonucleotides and a template-like oligo wherein the template-like oligo includes at least a first portion and a second portion and at least a part of the first portion of the template-like oligo is complimentary to at least a part of the primer-like oligo, and the inhibitor further includes a section of DNA between about 3 to about 50 oligonucleotides having a 5-exo oligo region in which at least part of the 5-exo oligo is complimentary to at least a part of the second portion of the template-like oligo, the 5'-exo oligo hybridizes to at least part of the second template-like oligo downstream of where said primer-like oligo hybridizes to at least a part of the first portion of the template-like region, the total length of the template-like oligo is equal to or greater than the combined lengths of the primer-like oligo and the 5'-exo oligo.

In still another embodiment the DNA polymerase inhibitor further including a Flap region of DNA; the Flap region is at least one nucleotide long and said Flap region is located downstream of said 5'-exo oligo region. In one embodiment the inhibitor includes an exo-loop, which is at least one nucleotide long and is located between said template-like oligo and said 5'-exo oligo.

One embodiment the inhibitor includes a 5'-exo oligo backbone linkages between at least some neighboring nucleotide pairs, some of these pairs may be located at nucleotides −1, +1, +2 and +3.

In some embodiments at least some backbone linkages are comprised of bonds that are resistant to enzymatic hydrolysis these types of linkages can be selected from the group consisting of thiophosphate bonds, peptide bonds and alkylated phosphates and the like. In one embodiment at least some of the backbone linkages in the oligonucleotide are resistant to 5' exonuclease activity.

In another embodiment the inhibitor includes a Flap region joined to the 5' exo oligo of the inhibitor, the length of the Flap region ranges from a single nucleotide to an oligonucleotide of about 50 bases, in one embodiment the Flap region and the 5'-exo oligo are joined by an exonuclease resistant linkage.

In some embodiments the 3'-terminus nucleotide of the primer region is selected from the group of nucleotides consisting of a natural 2'-deoxynucleotide and a 2',3'-dideoxynucleotides.

Another embodiment is a method for formulating a thermally activatable PolA DNA polymerase complex comprising the steps of: adding a DNA polymerase inhibitor according any of the inhibitors described or inferred herein to a concentrated PolA DNA polymerase solution and incubating the resulting solution before initiating a PCR. In one embodiment, the inhibitor and polymerase in an appropriate buffer, are incubated together for about 5 or more minutes before the reaction is started. In one embodiment the assay may include 1 to 5 units/μL of concentrated PolA DNA polymerase, at an inhibitor to enzyme ratio of from about 1:1 to about 50:1, in another embodiment the ratio of PolA to inhibitor is about 1:1 to about 10:1, in still another embodiment the ratio of PolA to inhibitor is about 2:1 to 5:1.

Still another embodiment is the a method for formulating a hot-start PCR composition comprises the steps of: 1) adding an inhibitor according to the invention to an amplification reaction solution comprising a thermostable DNA polymerase and other required PCR components to a final concentration of about 1 to 10 nM at a low temperature, typically 4° C., for example; and 2) incubating the combined mixture for a sufficient amount of time, typically at least 5 min, to allow the inhibitor to bind to the polymerase.

Still another embodiment is a method of formulating a hot-start PCR composition comprises the steps: 1) adding a solution of a DNA polymerase inhibitor of the invention to a concentrated PolA DNA polymerase solution, typically PolA is present in the solution in an amount of about 1 to about 5 unit/μL, at an inhibitor to enzyme ratio of from about 1:1 to about 10:1, in one embodiment the ratio is about 1:1; and 2) incubating the resulting solution for at least 5 min to result in a thermally activatable PolA DNA polymerase complex; 3) adding the solution of the thermally activatable PolA DNA polymerase complex to a solution containing the rest of the required components for a PCR reaction.

Yet another embodiment is a method of conducting a PCR reaction on a thermal cycler comprising the steps of: 1) activating a hot-start PCR composition formulated according to the methods of formulating a hot-start PCR composition disclosed herein by maintaining the composition at a temperature of from about 50° C. to about 99° C. for about 5 seconds and 2) carrying out the PCR reaction by having about 20 to about 99 PCR cycles wherein within each PCR cycle about 5 seconds is spent at about 95° C. for the denaturing step and about 5 to about 60 seconds spent at about 60° C. for the annealing and chain extension steps.

Still another embodiment is a kit for carrying out PCR, comprising: an inhibitor which includes any of the inhibits described or inferred herein, a thermostable polymerase, optionally at least one additional reagent can be added to the kit these reagents include, but are not limited to, the group consisting of, sterile water, 2'-deoxynucleoside triphosphates, $MgCl_2$, buffer, preservative, and the like In one embodiment of the invention, (referring now to FIG. 7 formula 1), the DNA polymerase inhibitor has the primary structure of formula 1, wherein the inhibitor is a single oligonucleotide comprising two sets of internally complimentary sequences, each capable of self-folding into a stem at lower temperatures. One of the self-hybridized stems, formed by the 3'-half of the sequence, is designed to interact with the Pol domain of a thermostable DNA polymerase enzyme by mimicking a normal primer-template hybrid; the other stem, which is formed by the 5'-half of the sequence and has an unhybridized 5'-end overlapping Flap region, may bind to the 5'-3' exonuclease domain by acting as an enzymatically uncleavable substrate of the exonuclease activity of the enzyme.

In another embodiment of the invention, (referring now to FIG. 7 formula 2), the inhibitor has a primary structure according to formula 2, wherein the inhibitor comprises two oligonucleotides, which at lower temperatures hybridize to form a secondary structure similar to that formed by the oligonucleotides illustrated in FIG. 7 formula 1, except that the loop portion for the Pol domain-binding stem is absent.

In still another embodiment of the invention, (referring now to FIG. 7 formula 3) the inhibitor has a primary structure illustrated in formula 3, wherein the inhibitor comprises two oligonucleotides, which at lower temperatures hybridize to form a secondary structure similar to that formed by the oligonucleotide illustrated in FIG. 7 formula 1, except that the loop portion for the exo domain-binding stem is absent.

In still another embodiment of the invention, (referring now to FIG. 7 formula 4), the inhibitor has primary structure illustrated in formula 4, wherein the inhibitor comprises three separate oligonucleotides, which at lower temperatures hybridize to form a secondary structure similar to that illustrated by formula 1 illustrated in FIG. 7, except that the loop portions for both the Pol domain-binding stem and the exo domain-binding stem are absent.

One aspect provides a method for turning the activity of a thermostable DNA polymerase on or off by using a temperature-sensitive inhibitor of a desired activation temperature for the polymerase. A particular use of the invention is for PCR including quantitative real-time PCR (qPCR), wherein the presence of a polymerase inhibitor according to the invention can suppress DNA amplification at room temperature during the reaction set-up time and thus significantly reduce nonspecific DNA amplification, and wherein the desired specific DNA amplification reaction can be readily initiated when the PCR composition is heated to the normal PCR temperature range, typically from about 50° C. to about 95° C.

One embodiment is a single oligonucleotide having the structure illustrated in FIG. 7, formula 1, wherein Pol Loop and Exo Loop are flexible linkers necessary to form the required secondary structure of the inhibitor; the primer-like oligo includes 8 to 50 bases; and 5'-Exo Oligo has about 3 to about 50 bases. In one embodiment nucleotides in the Pol Loop and Exo Loop are selected from the group consisting of natural oligonucleotides, unnatural oligonucleotides, aliphatic linkers, and a combination thereof. In one embodiment the inhibitor the Pol Loop and Exo Loop are comprised of nucleotides selected from the group including natural oligonucleotides having about from 4 to about 10 bases. In still another embodiment the Pol Loop and Exo Loop are comprised of natural oligonucleotides having at least 4 bases. In another embodiment, the 3'-terminus nucleotide of primer-like region is 2',3'-dideoxynucleotide; and the primer-like region has 8 to about 20 bases; 5'-exo oligo has 3 to about 15 bases. In one embodiment the template-like region includes one or more abasic sites.

Still another embodiment is an oligonucleotide as illustrated in FIG. 7 formula 2, in some embodiments the Exo Loop including at least one nucleotide is selected from the group consisting of natural oligonucleotides, unnatural oligonucleotides, aliphatic linkers, and any combination thereof; the primer-like region has about 8 to about 50 bases; and the 5'-Exo Oligo region has about 3 to about 50 bases. In one embodiment the Exo Loop is a natural oligonucleotide having about 4 to about 10 bases. In still another embodiment the Exo Loop is a natural oligonucleotide having about 4 bases. In one embodiment the 3'-terminus nucleotide of primer-like region is a natural 2'.3'-dideoxynucleotide; the primer-like oligo includes about 15 to about 20 bases; the 5'-exo oligo includes about 5 to about 10 bases. In one embodiment the template-like oligo comprises one or more abasic sites.

Yet another embodiment is a DNA polymerase inhibitor having the primary structure illustrated in FIG. 7 formula 3: wherein the Pol Loop is comprised of nucleotides selected from the group of natural oligonucleotides, unnatural oligonucleotides, aliphatic linkers, and a combination thereof; the primer-like region includes about 8 to about 50 bases; and the 5'-Exo Oligo region includes about 5 to about 50 bases. In one embodiment the Pol Loop is a natural oligonucleotide having about 4 to about 10 bases. In another embodiment the Pol Loop is a natural oligonucleotide having about 4 bases. In one embodiment the 3'-terminus nucleotide of primer-like oligo is a 2',3'-dideoxynucleotide; the primer-like oligo includes about 8 to about 20 bases; and 5'-exo oligo includes about 5 to about 20 bases. In one embodiment the template-like region comprises one or more abasic sites.

Another embodiment is the inhibitor having the primary structure illustrated in FIG. 7 formula 4; wherein the primer-like oligo includes about 8 to about 50 bases; and the 5'-Exo oligo includes about 5 to about 50 bases. In one embodiment the 3'-terminus nucleotide of the primer-like region is a natural 2',3'-dideoxynucleotide; the primer-like region includes about 15 to about 20 bases; and the 5'-exo oligo includes about 5 to about 20 bases. In another embodiment, the template-like region comprises one or more abasite sites.

Various other aspects and advantages of present invention will be apparent in the following detailed description

DESCRIPTION OF THE DRAWINGS

FIG. 1. When substrate-bound, Taq DNA polymerase exhibits two distinct conformations depending on if there is an additional single stranded DNA or RNA annealed to down-stream of the template. When there is no single stranded DNA or RNA annealed down-stream of the template (FIG. 1A), the exonuclease (5'-3' exonuclease) domain stays away from the template; when there is a single stranded DNA or RNA annealed to down-stream of the template (FIG. 1B), the 5'-3' exonuclease domain is drawn to the template, cleaving the single stranded DNA or RNA in front of the polymerase.

FIG. 2. Secondary structures of inhibitors according to some embodiments of the present invention: A) secondary structure formed from a primary structure of formula 1; B) secondary structure formed from a primary structure of formula 2; C) secondary structure formed from a primary structure of formula 3; and D) secondary structure formed from a primary structure of formula 4.

FIG. 3. Temperature-dependent conformation change switches on or off the inhibitory activity of the inhibitor. At temperature higher than $T_{act}$, the Exo-binding stem melts, causing the 5'-3' exonuclease domain to swing away from the template and subsequently to dissociate from the inhibitor due to the overall lowered binding affinity between the polymerase and the oligonucleotide inhibitor.

FIG. 4. Comparison of PCR products between using a non-hot-start method with a regular Taq DNA polymerase and using a hot-start method according to some embodiments of the present invention as revealed by agarose gel electrophoresis, where at the bottom of the gel image "Taq" and "HS Taq" denote DNA products from amplification reactions carried out with various units of regular Taq and hot-start Taq (NI17-5/Taq) according to the present invention, respectively, and "M" denotes DNA molecular weight marker from Invitrogen, Co. (Calsbad, Calif.). All amplifications were made from a 0.5 kb fragment from human genomic DNA. Amplifications run with regular Taq produced non-specific products as indicated by the widely diffused lower molecular band, while hot-start PCR using NI17-5/Taq according to the present invention generated a single band corresponding to the specific amplification product (See Example 3).

FIG. 7. A schematic illustration of the primary structure of some oligonucleotide DNA polymerase inhibitors designated as formulas 1, 2, 3 and 4, respectfully.

DETAILED DESCRIPTION

Figure 5:
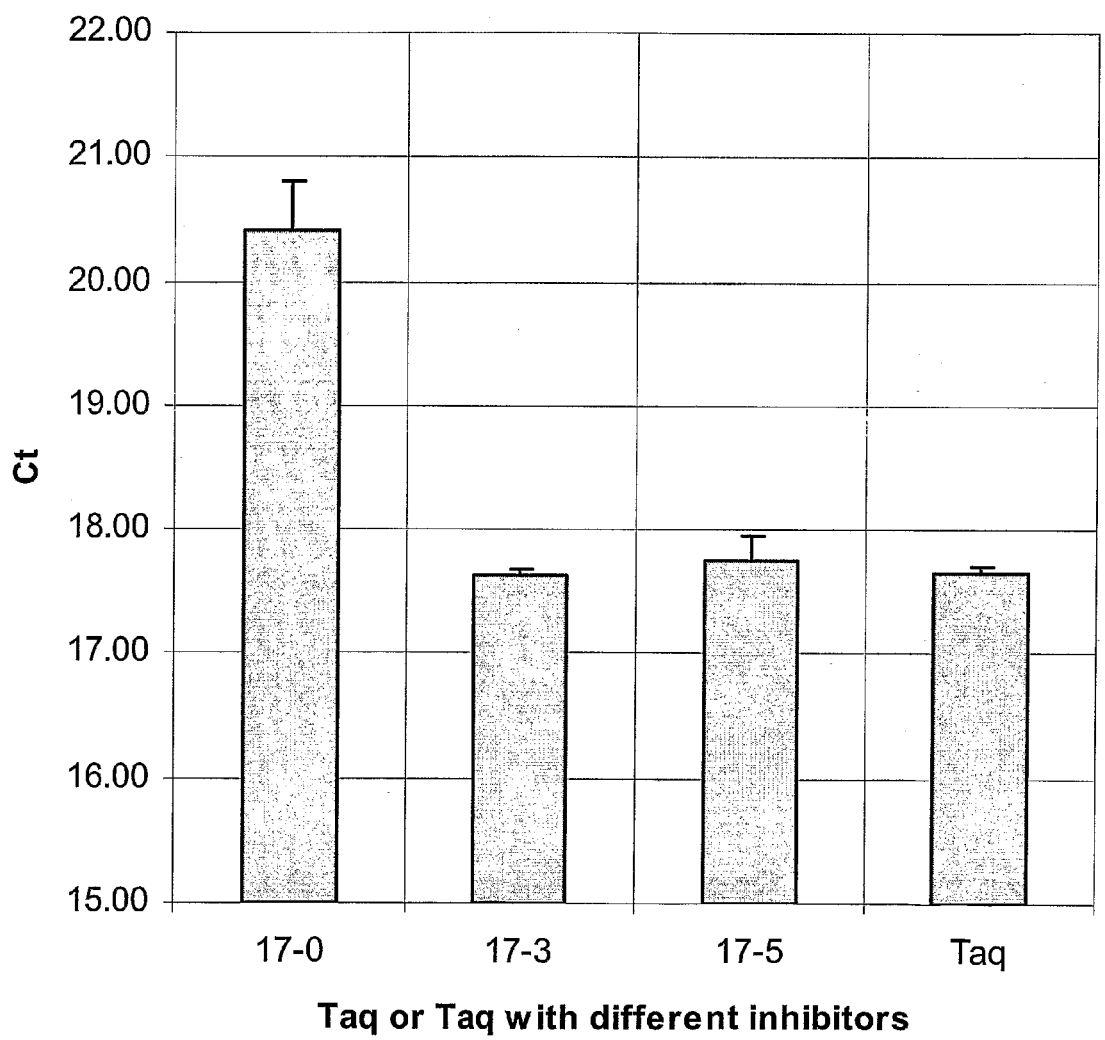
FIG. 5. Comparison of real-time PCR performance by regular Taq and various hot start Taq polymerases. In the figure, "NI17-5/Taq" and "NI17-3/Taq" represent hot-start enzymes prepared from inhibitor NI17-5 (SEQ ID No. 4) and Taq and inhibitor NI17-3 (SEQ ID No. 1) and Taq, respectively, according to Example 2; "NI17-0/Taq" represents a hot-start enzyme according to U.S. Pat. No. 6,830,902B1); and "Taq" represents regular non-hot-start Taq polymerase. Hot-start enzymes of the present invention gave a Ct as early as the Ct's for regular Taq, indicating that hot-start enzymes according to the present invention do not show significant PCR inhibition. On the other hand, hot-start enzyme NI17-0/Taq according to prior art gave a delayed Ct, suggesting that the enzyme preparation was inhibitory to PCR (See Example 4).

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

Definition of Terms used Herein

Unless noted otherwise terms used herein are given their usual and customary meaning as used in the art to which the various embodiments are directed.

The term "about" generally refers to range of plus or minus on the order of ten percent of the value the entire range being on the order of 20 percent of the relevant value.

The term "oligonucleotides", "oligo", "polynucleic acids" or "nucleic acids" are used interchangeably and refer to sequences of nucleic acids, 2'-deoxynucleic acids, peptide nucleic acids (PNA), locked nucleic acid (LNA) and other unnatural nucleic acids which include, but are not limited to, pyrazolo pyrimidine (Kutyavin, I et al. NAR 30, 2002:4952-4959; He J & Seela F, NAR 30, 2002:5485-5496), isoC, isoG (Johnson S C et al, Nucleic Acids Res. 2004 Mar. 29; 32(6): 1937-41) and combinations thereof.

A "primer" refers to an oligonucleotide, which is capable of acting as a starting point to extend along a complementary strand. Primers usually are used as a set in PCR, one forward and one reverse, wherein a forward primer contains a sequence complementary to a region of one strand of target nucleic acid and guides the synthesis of this strand, wherein the reverse primer contains a sequence complementary to the opposite stand of the target nucleic acid and guides the synthesis of the opposite strand of target nucleic acid.

"Hot start" refers to a practice in PCR or any DNA amplification where the amplification starts only after the reaction mixture has been heated to a certain temperature or above for a period of time. Since these temperatures are usually higher or hotter than room temperature at which the reactions are set up, the practice is referred to as "hot-start".

$T_m$ refers to the temperature at which 50% of the base pairs of a double stranded polynucleic acid, or a double-stranded portion of a polynucleic acid are dissociated under a given ionic strength and pH condition. Usually, longer base-pairing and/or higher GC content result in a higher $T_m$.

$T_{act}$ is the activation temperature of a thermostable PolA polymerase inhibited with an inhibitor according to the present invention. $T_{act}$ is closely and positively related to the melting temperature, $T_m$, of the Exo-binding stem. $T_{act}$ is generally lower than $T_m$, and typically falls within the range between about $T_m$ and a temperature about 30° C. lower than $T_m$. The higher the $T_m$, the higher the $T_{act}$ in general.

"Aptamers" refers to a class of oligonucleotide ligands as described in U.S. Pat. No. 5,693,502. These oligonucleotides are screened and isolated by an affinity exponential enrichment method. They typically exhibit certain secondary structures, which are believed to mimic the substrates or products of DNA polymerases.

PolA DNA polymerases refers to a group of type I DNA polymerases (Taq, Tth, etc.), each comprising a polymerase domain (Pol) for DNA polymerization, a 3'-5' exonuclease domain for proofreading, and a 5'-3' exonuclease domain (Exo) for clearing the synthesis path (Joyce C M et al. 1994 Annu Rev Biochem 63, 778-782).

"Pol domain" refers to the segment from amino acid #480 to amino acid #832 in Taq DNA polymerase or a similar segment in other Pol A family DNA polymerases. This domain houses the polymerase active site. (Lawyer F C et al 1989 JBC 264:6427-6437).

"Exo domain" refers to the protein segment from amino acid # 1 to amino acid #307 in Taq DNA polymerase or a similar segment in other PolA family DNA polymerases. This domain contains the 5'-3' exonuclease active site (Urs U K et al 1999 Acta Cryst D55, 1971-1977; Lawyer F C et al 1989 JBC 264:6427-6437). It is also referred to as 5' nuclease domain, which is responsible for removing RNA primers or damaged DNA nucleotides (Lyamichev V. et al. 1993, Science 260:778-783; Joubert A M et al 2003 J Bio Chem 278, 25341-25347).

"Competitive inhibitor" refers to a chemical that inhibits an enzyme by competing with a substrate for its active site. Typically, a competitive inhibitor and a related enzyme substrate share similar structure features.

The terms "deactivation" and "inactivation" are used interchangeably, and generally mean the suppression of polymerase activity or the activity of an inhibitor of the invention.

Some aspects of the present invention relate to the use of novel oligonucleotides as temperature-sensitive inhibitors for thermostable DNA polymerases. Some of these oligonucleotides exhibit temperature-dependent, and in some cases reversible inhibitory properties by changing the conformation of at least a portion of the oligonucleotides from double-stranded to single stranded or vice versa in a temperature-dependent manner. Some aspects of the invention also relate to the use of an oligonucleotide-based inhibitor in a hot-start PCR composition, wherein the inhibitor is capable of suppressing the activity of a thermostable DNA polymerase at or below a desired activation temperature, $T_{act}$, and wherein the inhibitor is thermally deactivated above $T_{act}$, thus liberating the polymerase activity and initiating the nucleic acid amplification process in a specific manner. Some embodiments of the invention further relates to a procedure for formulating the composition of a thermally activatable thermostable DNA polymerase complex and the composition of a hot-start PCR reaction mixture.

A typical PolA DNA polymerase such as Taq DNA polymerase is a protein consisting of three functional domains: a polymerase domain (Pol) for DNA polymerization, a 3'-5' exonuclease domain for proof-reading, and a 5'-3' exonuclease domain (Exo) for clearing the synthesis path (Joyce C M et al. 1994 Annu Rev Biochem 63, 778-782). A PolA polymerase may have only its Pol domain bound to a substrate or, when necessary, may have both the Pol domain and one of the 3'-5' exonuclease domain and 5'-3' exonuclease domain bound to their respective substrates. For example, a substrate for the Pol domain is typically a double-stranded DNA comprising a longer single-stranded DNA referred to as a template and a shorter complimentary single-stranded DNA referred to as a primer. A substrate for the 3'-5' exonuclease domain, however, is typically a mismatched or unhybridized 3'-end portion of an extended primer. On the other hand, a substrate for the 5'-3' exonuclease domain is typically a single-stranded oligonucleotide annealed to a template immediately downstream of an annealed primer. The oligonucleotide may be fully complementary or only partially complementary to the template sequence. Generally, a 5'-3' exonuclease tends to have higher activity toward an annealed oligonucleotide with an overhanging 5'-flap, which may be a single nucleotide or an oligonucleotide (Lyamichev, V. et al. 1993, Science 260:778-783). A substrate-bound PolA DNA polymerase may exhibit two different conformations, depending on the activity of the 5-Exo domain. If, for example, there is only a primer hybridized to a template with no exonuclease substrate present, only the Pol domain of Taq DNA polymerase binds to the primer-template hybrid while the two exonuclease domains stay away (FIG. 1A). On the other hand, if there is an additional single stranded DNA or RNA annealed to the same template but immediately downstream of where the Pol domain binds, the 5'-Exo domain is drawn towards the template to form a so-called "bifurcated duplex" conformation, followed by the cleavage of the single-stranded oligonucleotide to clear the pathway for the primer extension reaction (FIG. 1B).

An oligonucleotide of an aspect of the invention may function as a temperature-sensitive inhibitor for PolA DNA polymerases by binding to the enzymes via two different binding modes: a high affinity mode at lower temperatures and a low affinity mode at higher temperatures. In the high-affinity binding mode, the inhibitor binds to both the Pol domain and the Exo domain of the polymerase via a bifurcated duplex conformation without any enzymatic reactions occurring. In the low affinity mode, the inhibitor binds only to one of the two domains of the polymerase, making the inhibitor easily displaceable by a normal primer-template hybrid and thus initiating the desired DNA amplification reaction. The portion of the inhibitor binding to the Pol domain is typically an about 8- to about 50-base-paired double-stranded polynucleic acid comprising a primer-like oligonucleotide, referred to as PLO, hybridized to a template-like oligonucleotide, referred to as TLO. The 3'-terminus nucleotide of PLO is selected from a suitable natural 2'-deoxynucleotide or an unextendable nucleotide. An unextendable nucleotide is a nucleotide that is incapable of undergoing enzymatic extension reaction. An example of an unextendable nucleotide is a 2',3'-dideoxynucleotide. Preferably, the 3'-terminus nucleotide of PLO is 2',3'-dideoxynucleotide. For convenience, the PLO-TLO hybrid in the present invention will be referred to as the Pol-binding stem. Similarly, the Exo-binding portion of the inhibitor is also a double-stranded polynucleic acid comprising an about 3- to about 50-base oligonucleotide, called 5'-exo oligo, hybridized to the same TLO as for PLO but immediately downstream of the Pol-binding hybrid. Likewise, for convenience, the 5'-exo oligo-TLO hybrid in the present invention will be referred to as the 5'-Exo-binding stem. In general, the 5'-exo oligo has structural features that render the oligonucleotide unhydrolyzable by the 5'-3' exonuclease yet still capable of hybridizing to TLO. Methods for synthesizing enzymatically unhydrolyzable oligonucleotides are well known. One of the methods, for example, is to replace the normal backbone phosphate with a thiophosphate (Ott, J and Eckstein F, Biochemistry 26:8237-8241, 1987). Another method is to replace the backbone phosphate bond with a peptide bond (Slaitas A, et al, Nucleosides, Nucleotides, Nucleic Acid 22:1603-1605, 2003). At least the backbone linkage between the −1 nucleotide and the +1 nucleotide is enzymatically uncleavable, wherein "−1 nucleotide" denotes the 5'-side nucleotide of the main enzymatic target cleavage site and "+1 nucleotide" denotes the 3'-side nucleotide of the main enzymatic target cleavage site. In one embodiment, at least both the backbone linkage between the −1 nucleotide and +1 nucleotide and the backbone linkage between the +1 nucleotide and +2 nucleotide are enzymatically uncleavable, wherein "+2 nucleotide" denotes the second nucleotide from the main enzymatic target cleavage site on the 3'-side. In another embodiment, at least all three backbone linkages between each neighboring pair of nucleotides selected from −1, +1, +2 and +3 nucleotides are enzymatically uncleavable. In still another embodiment, the 5'-end of the hybridized 5'-exo oligo is attached, via an enzymatically uncleavable bond, with an overhanging Flap portion selected from a single nucleotide and an oligonucleotide having 2 to about 50 bases. Preferably, the flap regime may comprise a single nucleotide or an oligonucleotide having 2 to about 20 nucleotides. In one embodiment the flap is a single nucleotide or an oligonucleotide having 2 to about 5 nucleotides. In another embodiment, Flap is a single nucleotide. It is known that 5'-3' exonuclease tends to have higher activity toward a substrate having an unpaired nucleotide or unpaired oligonucleotide at the 5'-end (Lyamichev, V. et al. 1993, Science 260:778-783). By incorporating the same structural feature, some inhibitors of various embodiments of the invention generally have enhanced binding to the polymerase. A PolA DNA polymerase inhibitor with enhanced affinity according to some embodiments of the present invention can be used to suppress the activity of a PolA polymerase at a relatively low temperature such as room temperature at a very low concentration, typically in a range from about 0.5 nM to about 50 nM, thus making it less likely for the inhibitor to interfere with the PCR process. One can readily appreciate this particular advantage by comparing the PCR working concentrations for inhibitors of some embodiments of the present invention with those for aptamer-based DNA polymerase inhibitors or other similar oligonucleotide-based DNA polymerase inhibitors, which typically have working concentrations in the micromolar concentration range.

The temperature dependency of the inhibitor-enzyme interaction may be due to the fact that both enzyme-binding regions of the inhibitor have to assume a double-stranded conformation in order to maintain the activity of the inhibitor. Thus, a change of conformation from a double stranded to a single-stranded conformation for either region of the inhibitor will significantly diminish the affinity of the inhibitor for the enzyme. In general, loss of the double-stranded conformation for any one enzyme-binding region, either the Exo-binding stem or the Pol-binding stem, of the inhibitor is sufficient to re-activate the enzyme. In the low affinity mode, the inhibitor binds to the enzyme weakly and as a result can be readily displaced by a normal primer-template hybrid present in a PCR composition, leading to the start of a DNA polymerization reaction. In practice, even partial melting of the 5'-Exo-binding domain can sufficiently weaken the affinity of the inhibitor for the enzyme and therefore re-activate the enzyme. Consequently, as described in more details later, enzyme activation according to the invention generally occurs at or below the melting temperature of any of the two stems in the inhibitor.

Compared with the existing hot-start PCR methods, PCR method according to various embodiments of the present invention has several advantages. First, hot-start PCR according to the present invention are significantly more economical to practice than presently used techniques because the oligonucleotide-based inhibitors can be manufactured very inexpensively. Second, the double-stranded stems of the inhibitor, the required conformation for enzyme inhibition, can rapidly change to a single-stranded, noninhibitory conformation when the temperature is raised to or above the desired activation temperature. Consequently, hot-start process of the present invention takes much shorter time to complete. And third, at least some of the inhibitors according to the invention are thermally deactivated in an irreversible fashion. This irreversible deactivation coupled with the low working concentration of the inhibitor, typically in the nanomolar concentration range, make the inhibitors of the invention much less likely to interfere with the PCR process than other known inhibitors.

Referring now to FIG. 7 formula 1, in one embodiment of the invention the oligonucleotide-based inhibitor is a single oligonucleotide having a primary structure as shown in formula 1:

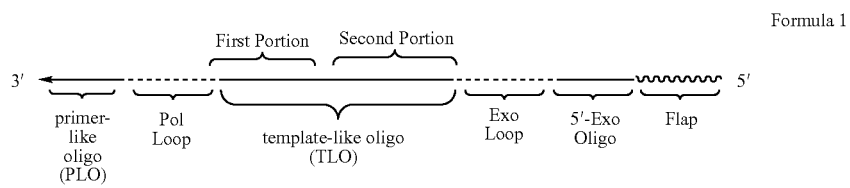

Formula 1 wherein the oligonucleotide comprises a total of 6 segments linked in tandem in the order of: 1) Flap; 2) 5'-Exo Oligo; 3) Exo Loop; 4) TLO; 5) Pol Loop; and 6) PLO, in the 5' to 3' direction; the covalent linkages between each neighboring pair of segments may be a phosphate bond, thiophosphate bond, amide bond, urea bond, urethane bond, thiourea bond or other similar bonds except for the linkage between the Flap segment and the 5'-Exo Oligo segment, which is required to be an enzymatically uncleavable bond selected from the group including but not limited to a thiophosphate bond, an alkylated phosphate bond and a peptide bond; the 5'-Exo Oligo and the 5'-side of TLO segment have complementary sequences that enable the two oligonucleotide segments to form the Exo-binding stem with the Exo Loop segment being the loop; similarly, PLO segment and the 3'-side of TLO segment are complementary and thus are capable of forming another stem, the Pol-binding stem, with the Pol Loop segment being the loop; PLO has 8 to about 50 bases, preferably 8 to about 20 bases; the hybridizing portion of 5'-Exo Oligo has 3 to about 50 bases, preferably 3 to about 15 bases; FIG. 2A shows the secondary structure of the inhibitor in its active form.

In this embodiment, the two loop segments, Pol Loop and Exo Loop, link the PLO segment and the 5'-Exo Oligo segment, respectively, to the TLO segment, and in general can be made of any flexible linkers including, but not limited to, natural or unnatural oligonucleotides, aliphatic linkers such as polyethylene glycols (PEG), or a combination thereof. Preferably, the loops can be constructed and incorporated into the inhibitor molecule on an oligonucleotide synthesizer using standard phosphoramidite chemistry. The lengths of the loops should generally be such that they do not negatively affect the formations of the two stem structures. For example, when the loops are oligonucleotides, they are generally a loop of about 4 to about 10 bases.

Referring now to FIG. 7 formula 2 in another embodiment of the invention, the inhibitor comprises in an about 1:1 molar ratio two separate oligonucleotides: 1) Flap-5'-Exo oligo-Exo Loop-TLO and 2) PLO, wherein the longer oligonucleotide comprises four covalently linked segments, Flap, 5'-Exo oligo, Exo Loop and TLO, arranged in the 5'-3' direction. The primary structure and composition of the inhibitor according to this embodiment are shown in FIG. 7 formula 2:

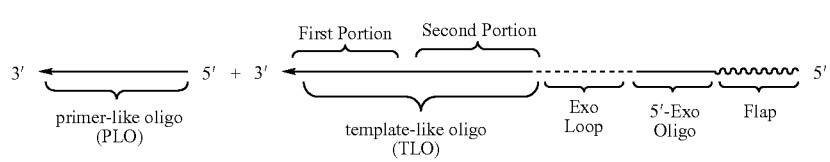

Formula 2 wherein PLO has 8 to about 50 bases, preferably about 15 to about 20 bases; 5'-exo oligo has 3 to about 50 bases, preferably about 5 to about 10 bases; other oligonucleotide segments in FIG. 7 formula 2 have the same definitions including definitions for the preferred embodiments as the corresponding ones in FIG. 7 formula 1 have. FIG. 2B shows the secondary structure of the inhibitor illustrated in FIG. 7 formula 2.

Referring now to FIG. 7 formula 3, in still another embodiment of the invention, the inhibitor comprises in an about 1:1 molar ratio two separate oligonucleotides: 1) Flap-5'-Exo oligo connected in the 5'-3' direction; and 2) TLO-Pol Loop-PLO also connected in the 5'-3'. The primary structure and composition of the inhibitor according to this embodiment are shown in FIG. 7 formula 3:

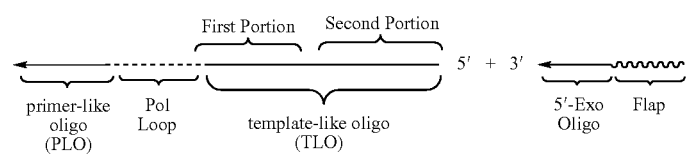

Formula 3

The hybridizing portion of 5'-Exo oligo has about 5 to about 50 bases, preferably 5 to about 20 bases. The remaining oligonucleotide segments in formula 3 have the same definitions including definitions for the preferred embodiments as the corresponding ones illustrated in FIG. 7 formula 3 in formula 1 have. FIG. 2C shows the secondary structure of the inhibitor according to formula 3.

In yet another embodiment of the invention, referring now to FIG. 7 formula 4, the inhibitor comprises in an about 1:1:1 ratio three separate oligonucleotides: 1) Flap-5'-Exo Oligo; 2) TLO; and 3) PLO. The primary structure and composition of the inhibitor according to this embodiment are shown in FIG. 7 formula 4:

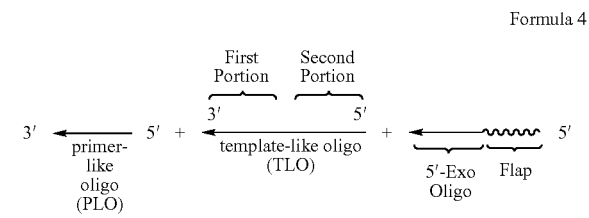

Formula 4 wherein PLO has 8 to about 50 bases, preferably about 15 to about 20 bases; 5'-exo oligo has about 5 to about 50 bases, preferably about 5 to about 20 bases; TLO and Flap in FIG. 7 formula 4 have the same definitions including definitions for the preferred embodiments as the corresponding segments in FIG. 7 formula 1 have. Similarly, the Flap portion may or may not be present. Preferably, it is present and preferably it is a nucleotide or an oligonucleotide having two to about 20 bases, preferably two to about 5 bases. FIG. 2D shows the secondary structure of the inhibitor according to FIG. 7 formula 4.

The activation and de-activation of a thermostable PolA polymerase according to the invention can be reversible or irreversible depending on the composition of the inhibitor. In general, a displaced inhibitor having the composition of formula 1 where the 3'-terminus nucleotide is an unextendable nucleotide such as 2',3'-dideoxynucleotide can easily fold back into the active form of the inhibitor again once the temperature is lowered. Such reversible inhibition is facilitated by the single-nucleotide construction of the inhibitor, where conformation change results in a relatively small entropy difference compared to inhibitors constructed of more than one oligonucleotide. It is generally understood that, if the 3'-terminus nucleotide is a regular extendable 2'-deoxynucleotide, an inhibitor according to FIG. 7 formula 1 may or may not be a reversible inhibitor, depending on if PLO becomes enzymatically extended during the enzyme activation process. For example, if the 5'-Exo-binding stem melts before the Pol-binding stem does during enzyme activation, PLO may be enzymatically extended into where 5'-Exo oligo binds, thus making it impossible for 5'-Exo oligo to fold back again when the temperature is lowered. Inhibitors constructed of multiple oligonucleotides according to FIG. 7 formulas 2, 3 and 4 are in general less reversible than the single oligonucleotide-based inhibitors according to FIG. 7 formula 1 with inhibitors according to FIG. 7 formula 4 having the least reversibility. The lower reversibility of these inhibitors is largely due to a significant entropy gain associated with the meltings of the inhibitors. For the purpose of the commonly practiced hot-start PCR applications, it is desirable to employ a highly irreversible inhibitor so that enzyme activation will be more facile. On the other hand, a highly irreversible inhibitor constructed of multiple oligonucleotides is relatively more complex to formulate and generally less stable. As a result, inhibitors according to FIG. 7 formulas 2 and 3 are preferable for use in hot-start PCR applications by having an optimal combination of simplicity and the ability to fast start a PCR reaction.

The activation temperature, $T_{act}$, of a thermostable DNA polymerase inhibited by an inhibitor according to the invention is closely related to the melting temperature, $T_m$, of the shorter stem in the inhibitor. For the purpose of the present invention, the temperature at which 50% of the inhibited polymerase is activated is defined as $T_{act}$. In general, even partial melting of the shorter stem can sufficiently weaken the overall interaction between the enzyme and the inhibitor, causing the inhibitor to be displaced by a normal primer-template hybrid and thus leading to the activation of the enzyme. As a result, $T_{act}$ is generally lower than the $T_m$ of the shorter stem of the inhibitor. Typically, $T_{act}$ is in a range between $T_m-30°$ C. and $T_m$. More typically, $T_{act}$ is between $T_m-20°$ C. and $T_m$. In general, the higher the $T_m$ of the shorter stem is, the higher $T_{act}$ is. Since the melting temperature of a double-stranded polynucleic acid is a function of the length and relative GC content of the polynucleic acid, the $T_m$ of the shorter stem of an inhibitor can be easily adjusted to any desired number by using common nucleic acid synthesis techniques. Thus, based on the positive correlation between $T_{act}$ and the $T_m$ of the shorter stem, $T_{act}$ can also be fine-tuned to a desired value accordingly.

It is understood to one skilled in the art that inhibitors of the invention and related concepts can be readily applied to any applications wherein a thermostable polynucleic acid polymerase is used and wherein it is desirable to have the enzyme activity turned off at a lower temperature and on at a higher temperature. Thermostable polynucleic acid polymerases include, but are not limited to, PolA DNA polymerases and any hybrid DNA polymerases comprising, for example a Pol B DNA polymerase covalently linked to a 5'-3' exonuclease domain of a PolA DNA polymerase, or to a similar enzyme such as FEN (Harrington J J, EMBO J. 1994 Mar. 1; 13(5): 1235-46.). In particular, inhibitors of the invention can be used in conjunction with numerous PCR protocols, including but not limited to standard PCR, RT-PCR, in-situ PCR, and quantitative PCR (qPCR). In addition, this invention can also be incorporated into other hot-start technologies. For example, a hot-start composition may comprise Taq, Pfu, and an inhibitor of the invention, wherein the inhibitor serves to hot-start Taq and an anti-Pfu antibody serves to hot start Pfu.

It is further understood to one skilled in the art that oligonucleotide-based inhibitors of the invention can be modified using known techniques so that they are less likely to interfere with a PCR process by serving as undesired primers or templates. One example of making modified oligonucleotides is to replace one or more nucleotides with unnatural or modified nucleotides such as abasic site (I. G. Shishkina and F. Johnson, Chem Res Toxicol, 2000, 13:907-912.), pyrimidine dimer (Taylor, J S & Brockie, I R, Nucleic Acids Res. 1988, 16:5123-5136.), isoC or isoG (Johnson S C et al, Nucleic Acids Res. 2004 Mar. 29; 32(6):1937-41), dyes (e.g. acridine, biotin, or Dabcyl), or various combination thereof. Alternatively or in combination with the above technique, various phosphate-backbone-mimicking linkers may be used to replace the natural phosphate bond linkages.

In one embodiment of the invention, a method of formulating a thermally activatable PolA DNA polymerase complex comprises the steps of: 1) adding a solution of an inhibitor of the invention to a concentrated PolA DNA polymerase solution, typically at 1 to 5 units/μL, at an inhibitor to enzyme ratio of from about 1:2 to about 50:1, preferably from about 1:1 to about 2:1, more preferably about 1:1; and 2) incubating the resulting solution for at least 5 minutes In another embodiment, a method of formulating a hot-start PCR composition comprises the steps of: 1) adding an inhibitor of the invention to an amplification reaction solution comprising a thermostable DNA polymerase and other required PCR components to a final concentration of 1 to 10 nM at a low temperature, typically 4° C., for example; and 2) incubating the combined mixture for a sufficient amount of time, typically at least 5 minute.

Still another embodiment of the present invention is, a method of formulating a hot-start PCR composition comprises the steps of: 1) adding a solution of the inhibitor of the invention to a concentrated PolA DNA polymerase solution, typically at 1 to 5 unit/μL, at an inhibitor to enzyme ratio of from about 1:1 to about 10:1, preferably about 1:1; and 2) incubating the resulting solution for at least 5 to result in a thermally activatable PolA DNA polymerase complex; 3) adding the solution of the thermally activatable PolA DNA polymerase complex to a solution containing the rest of the required components for a PCR reaction.

In yet another embodiment of the invention, a method of conducting a PCR reaction on a thermal cycler comprises the steps of: 1) activating a hot-start PCR composition according to aspects of the present invention by maintaining the composition at a temperature of from about 80° C. to about 100° C. for about at least 5 seconds; and 2) carrying out the PCR reaction by having about 19 to about 60 PCR cycles wherein within each PCR cycle about 5 seconds is spent at about 95° C. for the denaturing step and about 5 to about 60 seconds spent at about 60° C. for the annealing and chain extension steps.

Aspect of the present invention also relates to kits comprising required components for practicing the invention. In general, a kit of the invention comprises an inhibitor of the invention, a thermostable polymerase, and one or more reagents such as primers, deoxynucleoside triphosphates, $MgCl_2$, an enzyme-stabilizing agent and an appropriate buffer for performing an amplification reaction.

Having generally described the invention, the same will be more readily understood by reference to the following examples, which are provided only for illustrative purposes and not to limit the scope of the invention. Numerous embodiments of the invention within the scope of the claims that follow the examples will be apparent to those of ordinary skilled in the art from reading the foregoing text and following examples.

EXAMPLE 1

Oligonucleotides Inhibitors were generally synthesized on an Expedite 8909 Oligo Synthesizer (Applied Biosystems Inc, Foster City, Calif.) according to manufacturer's instructions using regular phosphoramidites of 2'-deoxynucleosides from Proligo, Boulder, Colo. or Glen Research, Sterling, Va. Cleavage of oligonucleotides from CPG support and deprotection were carried out by incubating the CPG beads in ammonium hydroxide at 55° C. for 16-18 hours according to manufacturer's suggestion. Once removed from the solid support, the oligonucleotides were concentrated down via a SpeedVac to remove the excess ammonia, and then purified by passing the concentrated oligonucleotides through a Sephadex G-25 column. The inhibitor oligos can also be custom-made from oligo-houses such as Sigma (St. Luis, Mo.) or IDT (Coralville, Iowa,)

The following oligonucleotide sequence (SEQ ID NO. 1) is an example of an inhibitor (NI17-3) according to formula 1 of the invention: 5'-T*G*G*GATATCCCTTTTCTTTCATT CTTACATATGTAAGAATGAAAGAAAA-3', wherein in the 5'- 3' direction the 5'-end T is Flap; the next GGG is 5'-Exo Oligo; ATAT is Exo Loop; CCCTTTTCTTTCATTCTTAC (nucleotides 9-28 of SEQ ID NO: 1) is TLO; the next ATAT is Pol Loop; GTAAGAATGAAAGAAAA (nucleotides 33-49 of SEQ ID NO:1) is PLO; and "*" indicates an enzymatically uncleavable thiophosphate backbone linkage. The oligonucleotide (SEQ ID NO: 1) folds into a secondary structure at below the enzyme activation temperature as shown below:

where thiolated phosphate bonds are between each pair of bold-faced letters.

EXAMPLE 2

One hundred μL of 1 μM exonuclease inhibitor (NI17-3) (SEQ ID No. 1, example 1) was mixed with 100 μL Taq DNA polymerase (5 unit/μL) in a reaction vessel. The solution was well mixed and then let stand at 4° C. for 5 minute. The Taq DNA polymerase-inhibitor complex thus formed is referred as NI17-3/Taq and serves as a hot-start Taq DNA polymerase in later examples.

EXAMPLE 3

Amplification reactions (100 μL) containing 0.5 μM each of forward primer, 5'-ACGCCTCCGACCAGTGTTT-3' (SEQ ID NO: 2), reverse primer, 5'-CTCGTCGCCCAC ATAGGA ATC -3'(SEQ ID NO: 3) were carried out in a PCR buffer containing 10 mM Tris, pH 8.0, 50 mM KCl, 2.5 mM MgCl$_2$, 2 mM each of dNTP, $10^3$ copies of human DNA and 2.5 units NI17-3/Taq which was prepared according to example 2. For comparison, control PCR reactions were carried out using the same PCR components as above except that NI17-3/Taq was replaced with a regular Taq. In both cases, reactions were first incubated at 50° C. for 30 minute to allow non-specific reactions, if any, to proceed, and then 95° C. for 3 seconds, followed by 35 cycles of PCR reactions with 5 seconds of denaturing at 95° C. and 30 seconds of annealing/extension at 60° C. for each cycle. The reaction products were analyzed by gel electrophoresis. As shown in FIG. 4, regular Taq generated DNA smears with DNA sizes significantly smaller than expected, indicating formations of predominantly non-specific products. On the other hand, PCR reactions employing NIHS-Taq generated a single specific band corresponding to the product of specific target amplification.

EXAMPLE 4

This example demonstrates that Taq inhibited with an inhibitor of the invention exhibits no or reduced activity at room temperature while recovering its full or near full activity in PCR, more specifically, in real time PCR.

Two different hot-start enzyme preps NI/Taq were prepared as described in example 2: the nucleotide inhibitor of NI17-5(SEQ ID NO: 4) has 17 base pairs in POL domain, and 5 base pairs in EXO domain; the nucleotide inhibitor of NI17-3(SEQ ID NO: 1) has 17 base pairs in POL domain, and 3 base pairs in EXO domain. As a control, the nucleotide inhibitor of NI17-0(SEQ ID NO: 5), consisting of 17 base pairs in POL domain but no base pairs in EXO domain, was also prepared according to the literature (US. Pat. No. 6,830, 902 B1). In each prep, Taq was 125 nM and the oligonucleotide was approximately 1 μM.

The first set of experiments compare NI17-5/Taq NI17-3Taq, NI17-O/Taq and Taq DNA polymerase in real time PCR reactions. Each enzyme prep was added to a final concentration of 2.5 nM in 100 μL, reactions containing 500 nM each of GAPDH forward primer (SEQ ID NO: 6) and reverse primers (SEQ ID NO: 7), 1μL, of human cDNA (Clontech, Mountain View, Calif.), 250 μM of dNTP in IX AmpliTaq Buffer with 1.5 mM MgCl$_2$, and 1× EvaGreen (Biotium, Hayward, Calif.). As shown in FIG. 5, NI17-5Taq,NI17-3/Taq were as active as regular Taq, as they all had similar Ct's, while NI17-0/Taq had delayed Ct.

Figure 6:
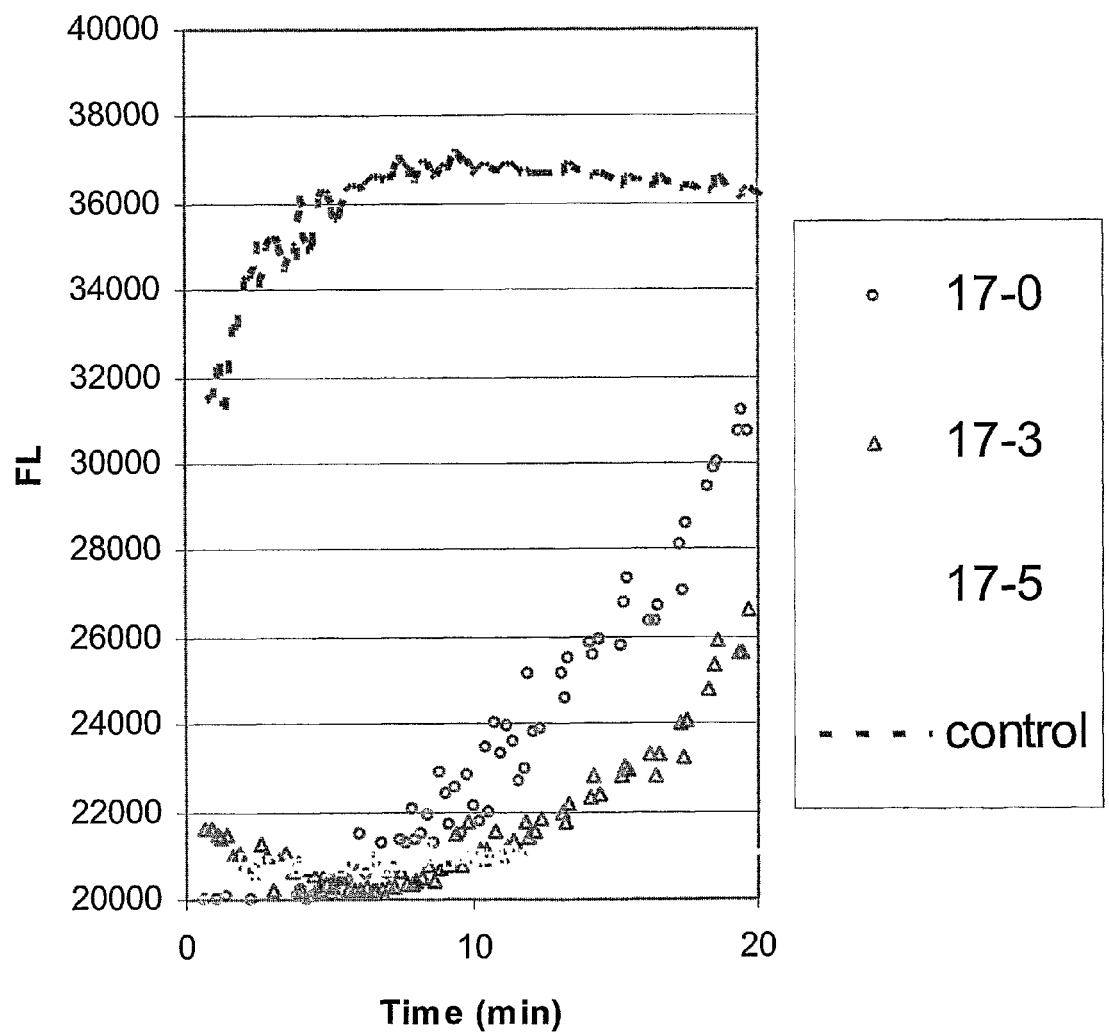
FIG. 6. Comparison of residual polymerase activities at 30° C. The same enzyme systems were used as in FIG. 5. Regular Taq exhibited residual activity at 30° C. as expected, while NI17-0/Taq, NI17-3/Taq and NI17-5/Taq showed significantly suppressed enzyme activity. The degree of enzyme inhibition by the inhibitors is in the order: NI17-5>NI17-3>NI17-0.

The second set of the experiment compares NI17-5/Taq, NI17-3/Taq, NI17-0/Taq and regular Taq DNA polymerase in activity assay at low temperature, specifically at 30° C. Again each enzyme prep was added to a final concentration of 2.5 nM in 100 μL reactions containing 20 nM M13 single stranded DNA 200 nM M13 forward primer (SEQ ID NO:8), 250 μM of dNTP in 1×AmpliTaq Buffer with 1.5 mM MgCl$_2$, and 1× EvaGreen (Biotium, Hayward, Calif.). As shown in FIG. 6, regular Taq showed the highest activity, while all Taq's with an inhibitor showed reduced or no activities. It is worth noting that, compared with Taq inhibited with a "stem-loop" type of inhibitor (NI17-0) as disclosed in prior art (US. Pat. No. 6,830,902 B1), Taq inhibited with an inhibitor of the present invention generally had less residual activity at below the PCR temperature while showing higher activity at real-time PCR temperature. It is further worth noting that the longer the length of the 5'-Exo oligo of the inhibitor according to the invention, the better the inhibitor suppresses residual enzyme activity at lower temperatures, as shown by the results on NI17-5/Taq and NI17-3.

Still, the common strategy is to suppress the enzyme activity at below the PCR operating temperature.

One strategy of developing a hot-start polymerase is to chemically modify the enzyme, more specifically, the lysine residues of the enzyme, with a thermally unstable chemical group to inactivate the enzyme. Once the reaction is heated to temperatures above 90° C. for 10 to 20 minutes, the heat-labile modifying group is cleaved from the enzyme, thus re-activating the enzyme activity. (U.S. Pat. Nos. 5,677,152 and 6,183,998). There are a couple of major drawbacks with this method. First, since there are multiple lysine residues in the enzyme, the modification reaction is difficult to control, typically resulting in a complex mixture of labeled enzyme with some enzyme molecules more heavily labeled and others lightly labeled. Accordingly, the temperature response of the modified enzyme molecules is often heterogeneous with the lightly labeled enzyme molecules more easily re-activated but the more heavily labeled enzyme molecules more difficult to be reactivated. Second, the yield for making the modified enzyme is relatively low, typically in the range of 10 to 50%, which, when coupled with the relatively high cost of the enzyme itself, can make this method uneconomical. Finally, it is desirable to shorten the 10- to 20-minutes enzyme activation time, which makes up a significant portion of the overall PCR time with this method.

Another hot-start PCR method employs polymerase-specific monoclonal antibodies to inhibit the enzyme activity. Often an antibody to enzyme molar ratio of seven to one is used to sufficiently inactivate the enzyme. The monoclonal antibodies bind to the polymerase at lower temperatures such as room temperature in a manner to inactivate the enzyme. When the reaction temperature is raised above 90° C., the antibodies lose affinity for the enzyme, which therefore becomes reactivated again. (U.S. Pat. No. 5,338,671, Scalice E R et al, Kellogg et al, (1994) Biotechniques 16:1134-1137). One advantage of this method is that the enzyme activation time is only 1 to 3 minutes, a significant improvement over the chemically modified enzyme method. However, a major drawback with this method is the relatively high cost associated with the use of a large amount of antibody molecules.

Still another hot-start PCR method employs negatively charged polymers to block polymerase as disclosed in the US. Pat. Application No. US2003/0092135A1. The negatively charge polymers exhibit temperature-dependent inhibition to Taq DNA polymerase activity with high inhibition at low temperatures and low or no inhibition at high temperatures.

Other variations of negatively charge polymers have also been used to inhibit DNA polymerase activity. For example, short DNA fragments (Kainz P. et al (2000) BioTechniques 28:278-282, also U.S. Pat. No. 6,830,902B1) or aptamers (U.S. Pat. No. 5,693,502) have been used to formulate hot-start PCR reactions. These oligonucleotide-based inhibitors bind to a DNA polymerase by mimicking the natural substrate of the enzyme. At elevated temperatures, the inhibitors lose their binding affinity for the enzyme, rendering polymerase available to its normal substrate. However, in order to achieve complete enzyme inhibition at lower temperatures, the concentration of the inhibitors typically needs to be in the hundreds of micromole range so that they can compete effectively for enzyme binding with the natural substrate. Although the hot-start method using these inhibitors also has the advantage of relatively short enzyme activation time, typically within a minute, the high cost of having to use a large quantity of the inhibitors makes this technology unpractical.

Inhibitors of the invention are highly potent while at the same time they are easily deactivated at higher temperatures with minimal or essentially no interference with the PCR process. By binding to both domains of the enzyme via a so-called bifurcated duplex mode, inhibitors according to the invention have a significantly higher enzyme-binding affinity than any previously known oligonucleotide-based inhibitors for a thermostable polymerase. As a result, inhibitors of the invention can be used at a very low concentration, typically about 1 nM to about 10 nM in a hot-start PCR composition. Once a PCR composition comprising an inhibitor of the invention is heated to sufficiently high a temperature, the stem moieties of the inhibitor melt into single stranded conformations, resulting in the loss of affinity between the inhibitor and the enzyme and thus liberating the enzyme activity. In most of the cases, the two stems in the inhibitor of the invention are not necessarily equal in length. As a result, the shorter stem is the first to begin conformation change when the temperature approaches its melting temperature. In general, significant conformation change of either the Pol-binding stem or the 5'-Exo-binding stem, but not necessarily both, is sufficient to weaken the inhibitor-enzyme interaction and thus cause the inhibitor to be displaced by a normal primer-template hybrid, leading to the enzyme activation. The facile inhibitor de-activation or equivalently, enzyme activation, at higher temperatures, coupled with the relatively low concentration requirement, make inhibitor of the invention ideal for use in hot-start PCRs. In general, inhibitors of the invention can sufficiently suppress DNA polymerase activity at a very low concentration, typically at from 1 nM to 10 nM, at lower temperatures such as room temperature while having insignificant inhibitory effect toward the PCR process The temperature at which 50% of the inhibited polymerase is activated is referred to as the enzyme activation temperature $T_{act}$, and is closely and positively related to the melting temperature $T_m$ of the shorter stem in the inhibitor of the invention. $T_{act}$ is generally lower than $T_m$, and typically falls within a range between $T_m$ and a temperature about 30° C. lower than $T_m$. The higher the $T_m$, the higher the $T_{act}$, in general. At ambient temperature, which is generally well under $T_{act}$, the inhibitor blocks the activity of a PolA DNA polymerase such as Taq by binding to both the Pol domain and the 5'-exonuclease domain of the enzyme via a bifurcated duplex conformation. Once the temperature of a PCR composition approaches the $T_m$ of the shorter stem in the inhibitor, the stem starts to melt and as a result the inhibitor becomes only loosely associated with the enzyme. The weakened association between the enzyme and inhibitor makes the latter easily displaceable by a normal primer-template hybrid, thus liberating the enzyme activity. Since the melting temperature of a double-stranded oligonucleotide is a function of the length and the relative GC content of the oligonucleotide, the $T_m$ of the shorter stem in the inhibitor can be easily adjusted to any desired temperature using common nucleic acid synthesis techniques. Consequently, the enzyme activation temperature $T_{act}$ can also be fine-tuned to a desired temperature accordingly.

All references, patents, patent applications and the like cited herein and not otherwise specifically incorporated by references in their entirety, are hereby incorporated by references in their entirety as if each were separately incorporated by reference in their entirety.

An abstract is included to aid in searching the contents of the application it is not intended to be read as explaining, summarizing or otherwise characterizing or limiting the invention in any way.

The present invention contemplates modifications as would occur to those skilled in the art. It is also contemplated that processes embodied in the present invention can be altered, duplicated, combined, or added to other processes as would occur to those skilled in the art without departing from the spirit of the present invention.

Further, any theory of operation, proof, or finding stated herein is meant to further enhance understanding of the present invention and is not intended to make the scope of the present invention dependent upon such theory, proof, or finding.

While the invention has been illustrated and described in detail in the figures, formulas and foregoing description, the same is considered to be illustrative and not restrictive in character, it is understood that only the preferred embodiments have been shown and described and that all changes and modifications that come within the spirit of the invention are desired to be protected.

What is claimed is:

1. A DNA polymerase inhibitor suitable for binding to a Pol domain and a 5'-exo domain of a DNA polymerase, said inhibitor comprising:
at least one oligonucleotide, said oligonucleotide including:
a first section of DNA, and a second section of DNA, wherein:
said first section comprises a primer-like oligonucleotide of about 8 to about 50 nucleotides, and further comprises an oligonucleotide complementary to said primer-like oligonucleotide, and wherein said first section of DNA forms a double stranded DNA structure capable of binding to the Pol domain of a DNA polymerase,
said second section comprises a 5'-exo oligonucleotide of about 3 to about 50 nucleotides and an oligonucleotide complementary to said 5'-exo oligonucleotide, and wherein said second section of DNA forms a double stranded structure capable of binding to the 5'-exo domain of said polymerase, and
said second section includes at least two nucleotides joined by a backbone linkage wherein at least one of said backbone linkages is resistant to 5'-exonuclease activity.

2. The DNA polymerase inhibitor according to claim 1, wherein the cumulative nucleotide count of the contiguous portion of DNA spanning the oligonucleotide complementary to said primer-like oligonucleotide and the oligonucleotide complementary to said 5'-exo oligonucleotide is greater than the sum of the lengths of the primer-like oligonucleotide and the 5'-exo oligonucleotide.

3. The DNA polymerase inhibitor according to claim 1, further including a Flap region of DNA, wherein said Flap region is at least one nucleotide long and said Flap region is located downstream of said 5'-exo oligonucleotide.

4. The DNA polymerase inhibitor according to claim 1, further including an exo-loop, wherein said exo-loop comprises at least one unpaired nucleotide located between said 5'-exo oligonucleotide and said oligonucleotide complementary to said 5'exo oligonucleotide.

5. The inhibitor according to claim 2, wherein the 5'-exo oligonucleotide backbone linkages between at least some neighboring nucleotide pairs are selected from the group of said neighboring nucleotide pairs consisting of nucleotides −1, +1, +2 and +3.

6. The inhibitor according to claim 1, wherein the 5'-exonuclease resistant backbone linkages include at least one linkage selected from the group consisting of thiophosphate bonds, peptide bonds and alkylated phosphates.

7. The inhibitor according to claim 3, wherein said Flap region ranges from a single nucleotide to an oligonucleotide of about 50 bases, and the Flap and the 5'-exo oligonucleotide are joined by at least one exonuclease resistant linkage.

8. The inhibitor according to claim 2, wherein the 3'-terminus nucleotide of said primer-like oligo is selected from the group of nucleotides consisting of natural 2'-deoxynucleotides and 2',3'-dideoxynucleotides.

9. A method of formulating a thermally activatable PolA DNA polymerase complex, comprising the steps of:
   adding a DNA polymerase inhibitor according to claim 1 to a concentrated PolA DNA polymerase solution; and
   incubating the resulting solution before initiating a reaction catalyzed by DNA polymerase.

10. A kit for carrying out PCR, comprising:
an inhibitor according to claim 1;
a thermostable DNA polymerase; and
at least one additional reagent selected from the group consisting of sterile water, 2'-deoxynucleoside triphosphates, $MgCl_2$, and buffer.

* * * * *

UNITED STATES PATENT AND TRADEMARK OFFICE
CERTIFICATE OF CORRECTION

PATENT NO. : 8,530,194 B2  Page 1 of 1
APPLICATION NO. : 12/088213
DATED : September 10, 2013
INVENTOR(S) : Mao et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1246 days.

Signed and Sealed this
Fifteenth Day of September, 2015

Michelle K. Lee
*Director of the United States Patent and Trademark Office*

SEQUENCE LISTING

<160> NUMBER OF SEQ ID NOS: 8

<210> SEQ ID NO 1
<211> LENGTH: 49
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Enzymatically uncleavable thiophosphate
      backbone linkage
<220> FEATURE:
<221> NAME/KEY: misc_feature
<222> LOCATION: (2)..(3)
<223> OTHER INFORMATION: Enzymatically uncleavable thiophosphate
      backbone linkage
<220> FEATURE:
<221> NAME/KEY: misc_feature
<222> LOCATION: (3)..(4)
<223> OTHER INFORMATION: Enzymatically uncleavable thiophosphate
      backbone linkage

<400> SEQUENCE: 1
tgggatatcc ttttctttc attcttacat atgtaagaat gaaagaaaa                 49

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acgcctccga ccagtgttt                                                 19

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctcgtcgccc acataggaat c                                              21

<210> SEQ ID NO 4
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Enzymatically uncleavable thiophosphate
      backbone linkage
<220> FEATURE:
<221> NAME/KEY: misc_feature
<222> LOCATION: (2)..(3)
<223> OTHER INFORMATION: Enzymatically uncleavable thiophosphate
      backbone linkage
<220> FEATURE:
<221> NAME/KEY: misc_feature
<222> LOCATION: (3)..(4)
<223> OTHER INFORMATION: Enzymatically uncleavable thiophosphate
      backbone linkage
<220> FEATURE:
<221> NAME/KEY: misc_feature
<222> LOCATION: (4)..(5)
<223> OTHER INFORMATION: Enzymatically uncleavable thiophosphate
      backbone linkage
<220> FEATURE:
<221> NAME/KEY: misc_feature
<222> LOCATION: (5)..(6)
<223> OTHER INFORMATION: Enzymatically uncleavable thiophosphate
```

```
        backbone linkage

<400> SEQUENCE: 4
tgcgggatat cccgctttc aaacattctt acatatgtaa gaatgtttga aaa        53

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 cccgctttc aaacattctt acatatgtaa gaatgtttga aaa                   43

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaaggtgaag gtcggagtc                                             19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaagatggtg atgggatttc                                            20

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgccagggtt ttcccagtca cgac                                       24
```